(12) United States Patent
Okamoto et al.

(10) Patent No.: US 7,609,803 B2
(45) Date of Patent: Oct. 27, 2009

(54) METHOD FOR ESTIMATING SCATTERED RAY INTENSITY IN X-RAY CT AND X-RAY CT APPARATUS

(75) Inventors: Yosuke Okamoto, Kanagawa-ken (JP); Naruomi Akino, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/244,259

(22) Filed: Oct. 2, 2008

(65) Prior Publication Data

US 2009/0092222 A1      Apr. 9, 2009

(30) Foreign Application Priority Data

Oct. 2, 2007     (JP) ............................ 2007-258987

(51) Int. Cl.
*A61B 6/00*     (2006.01)
(52) U.S. Cl. .......................................... 378/7; 382/131
(58) Field of Classification Search ............... 378/4–27, 378/86, 87, 901; 382/131
See application file for complete search history.

(56) References Cited

U.S. PATENT DOCUMENTS 6,163,589 A * 12/2000 Vartanian ........................ 378/7

FOREIGN PATENT DOCUMENTS

| JP | 11-299768   | 11/1999 |
| JP | 2006-334319 | 12/2006 |
| JP | 2007-111314 | 5/2007  |

* cited by examiner

*Primary Examiner*—Courtney Thomas
(74) *Attorney, Agent, or Firm*—Oblon, Spivak, McClelland, Maier & Neustadt, L.L.P.

(57) ABSTRACT

A method for estimating a scattered ray intensity distribution in an X-ray CT apparatus, the method includes: irradiating a subject with X-rays; and configuring a cross-sectional image of the subject by detecting the X-rays passing through the subject, on the basis of a path length of a scattered ray passing through the subject, an X-ray absorption coefficient of the subject and an X-ray scattering probability of the subject, intensity of the scattered ray being calculated.

20 Claims, 7 Drawing Sheets

METHOD FOR ESTIMATING SCATTERED RAY INTENSITY IN X-RAY CT AND X-RAY CT APPARATUS

CROSS-REFERENCE TO RELATED APPLICATIONS

This application is based upon and claims the benefit of priority from the prior Japanese Patent Application No. 2007-258987, filed on Oct. 2, 2007; the entire contents of which are incorporated herein by reference.

BACKGROUND OF THE INVENTION

1. Field of the Invention

This invention relates to a method for estimating scattered ray intensity distribution in X-ray CT from a shape of a subject and an X-ray CT apparatus.

2. Background Art

An X-ray CT apparatus detects intensity of X-rays (hereafter referred to as main ray) radiated from an X-ray bulb and going straight through a subject, and forms a cross-sectional image of the subject. At this time, detection of X-rays scattered from the subject (hereafter referred to as scattered ray) and the main ray produces a ghost image on the cross-sectional image resulting in degradation of image quality. Conventionally, the scattered ray incident from an oblique direction to a detector has been screened by placing a collimator beside the detector, but the scattered ray incident from normal to the detector has been unable to be separated. A technique simulating the scattered ray using a Monte Carlo method and removing the scattered ray component from an original signal configuring the image detected by the detector (e.g. JP-A 11-299768 (Kokai) (1999)) and a technique forming a correction data having the scattered component removed by simulation and configuring a high-precision image (e.g. JP-A 2006-334319 (Kokai)) are disclosed.

However, while a intensity distribution of the scattered ray can be estimated from a structure of the apparatus and a shape of the subject by simulating X-ray tracks by the Monte Carlo method, there has been a problem associated with taking a too long time for a purpose tracking only component incident to the detector to produce an error out of the scattered X-ray, because the Monte Carlo method tracks all scattering tracks. Therefore, application to subjects of all types of shapes has been difficult.

SUMMARY OF THE INVENTION

According to an aspect of the invention, there is provided a method for estimating a scattered ray intensity distribution in an X-ray CT apparatus, the method including: irradiating a subject with X-rays; and configuring a cross-sectional image of the subject by detecting the X-rays passing through the subject, on the basis of a path length of a scattered ray passing through the subject, an X-ray absorption coefficient of the subject and an X-ray scattering probability of the subject, intensity of the scattered ray being calculated.

According to another aspect of the invention, there is provided an X-ray CT apparatus including: a first X-ray generation section configured to generate X-rays; an X-ray detection section configured to detect the X-rays passing through a subject; an image reconfiguration section configured to configure a cross-sectional image of the subject on the basis of a result detected by the X-ray detection section; and a scattered ray calculation section configured to estimate a scattered ray intensity distribution of the X-rays in the subject, the scattered ray calculation section estimating the scattered ray intensity distribution by calculating intensity of the scattered ray on the basis of a path length of a scattered ray passing through the subject, an X-ray absorption coefficient of the subject and an X-ray scattering probability of the subject, and the image reconfiguration section reconfiguring the cross-sectional image by correcting the result detected by the X-ray detection section using the scattered ray intensity distribution estimated by the scattered ray calculation section.

DETAILED DESCRIPTION OF THE INVENTION

An embodiment of the invention will now be described with reference to the drawings.

Figure 1:
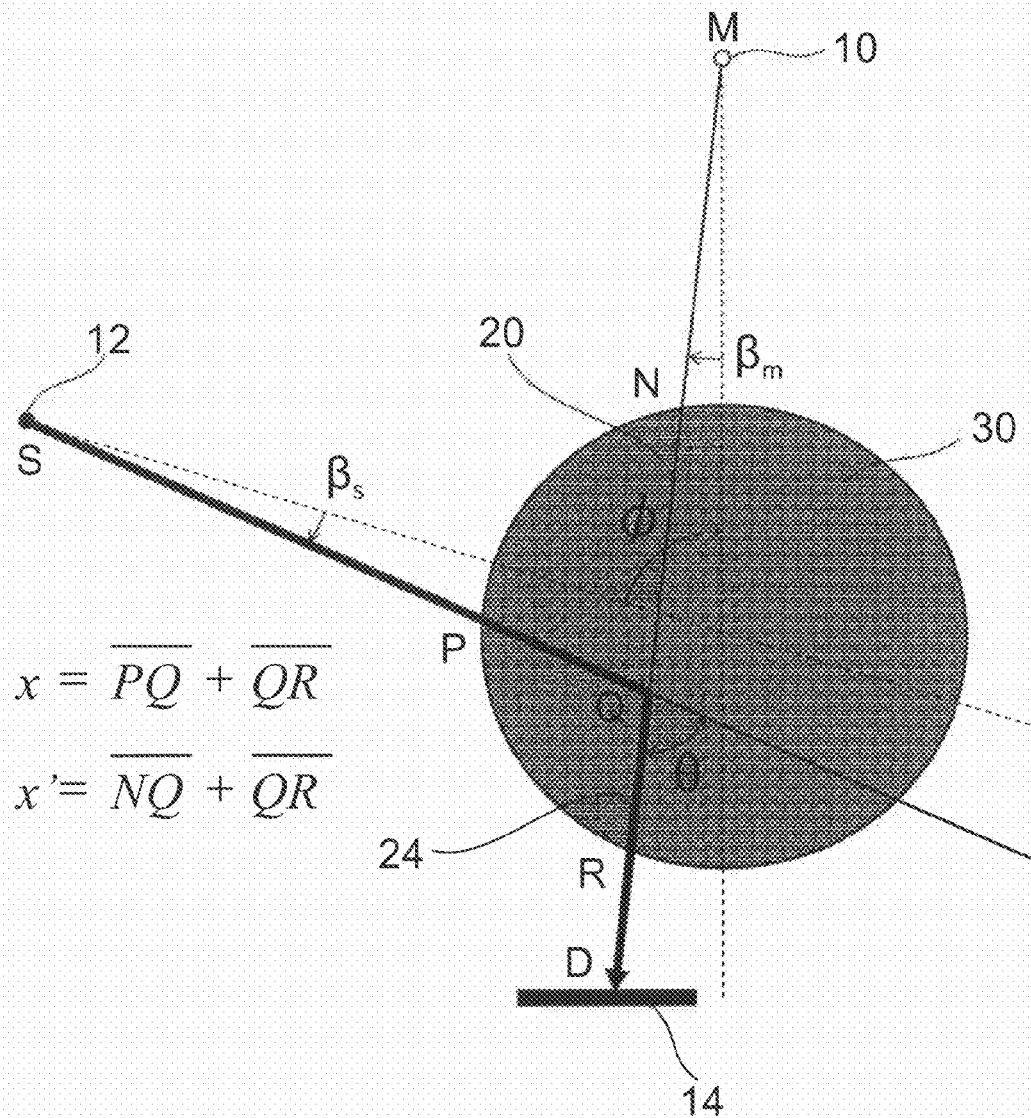
FIG. 1 is a schematic view describing a method for estimating a primary scattered ray intensity distribution according to an embodiment of the invention.

FIG. 1 is a schematic view describing a method for estimating a primary scattered ray intensity distribution according to the embodiment of the invention.

X-rays radiated from a first bulb (X-ray generation section) 10 located at a point M in a direction of an angle βm with respect to a center of a subject 30 is incident to the subject 30 at a point N. A transmission ray 20 passes through the subject 30 along a path NQR to a point R via a point Q and reaches a detector 14 at a point D on the detector 14. A path length x' of the transmission ray 20 in the interior of the subject 30 is given by a following equation.

$$x' = NQ + QR$$

Here, in an X-ray CT, besides the first bulb 10, a second bulb 12 generating X-rays can be provided. Besides the transmission ray 20 from the first bulb 10, the X-rays radiated from the second bulb 12 located at a point S in a direction of an angle φ with respect to the first bulb 10 viewed from the subject 30 is also scattered in the interior of the subject 30 to reach the detector 14. That is, a source of the scattered ray includes illustratively scattering of the X-rays radiated from the second X-ray bulb 12 provided besides the first bulb 10. A specific example provided with the second bulb 12 will be described.

The X-rays radiated from the second bulb 12 in a direction of an angle βs with respect to the center of the subject 30 is incident to the subject 30 at a point of P. A primary scattered ray 24 scattered once with a scattering angle θ at a point Q in the interior of the subject 30 passes through the subject 30 along a path PQR and reaches the detector 14 at the point D. A path length x of the primary scattered ray 24 is given by a following equation.

$$x = PQ + QR$$

The X-rays radially radiated from the second bulb 12 by varying βs are scattered in the interior of the subject 30 and the scattered rays are integrated to calculate the intensity of the primary scattered ray 24 at the point D. While the second bulb 12 is placed imaginarily to calculate the intensity of the scattered ray, it is possible to place it really to collect experimental data and compare estimated values with experimental values.

Assuming the intensity of the transmission ray 20 to be Ip and the intensity of the primary scattered ray 24 to be Is, an X-ray intensity I at the point D on the detector 14 is given by a following equation.

$$I = Ip + \Sigma Is$$

Here, the first term in a right side of the above equation is the intensity of the transmission ray 20 on the detector 14, and the second term in the right side is the intensity of the primary scattered ray 24 on the detector 14. Furthermore, varying the angle βs of the X-rays radiated from the first bulb 10 makes it possible to achieve the distribution of the primary scattered ray intensity ΣIs and the distribution of the intensity Ip of the transmission ray 24 on the detector 14 while scanning the position of the detection point D on the detector 14, moreover the distribution of the X-ray intensity I can be achieved as the sum of them.

Figure 2:
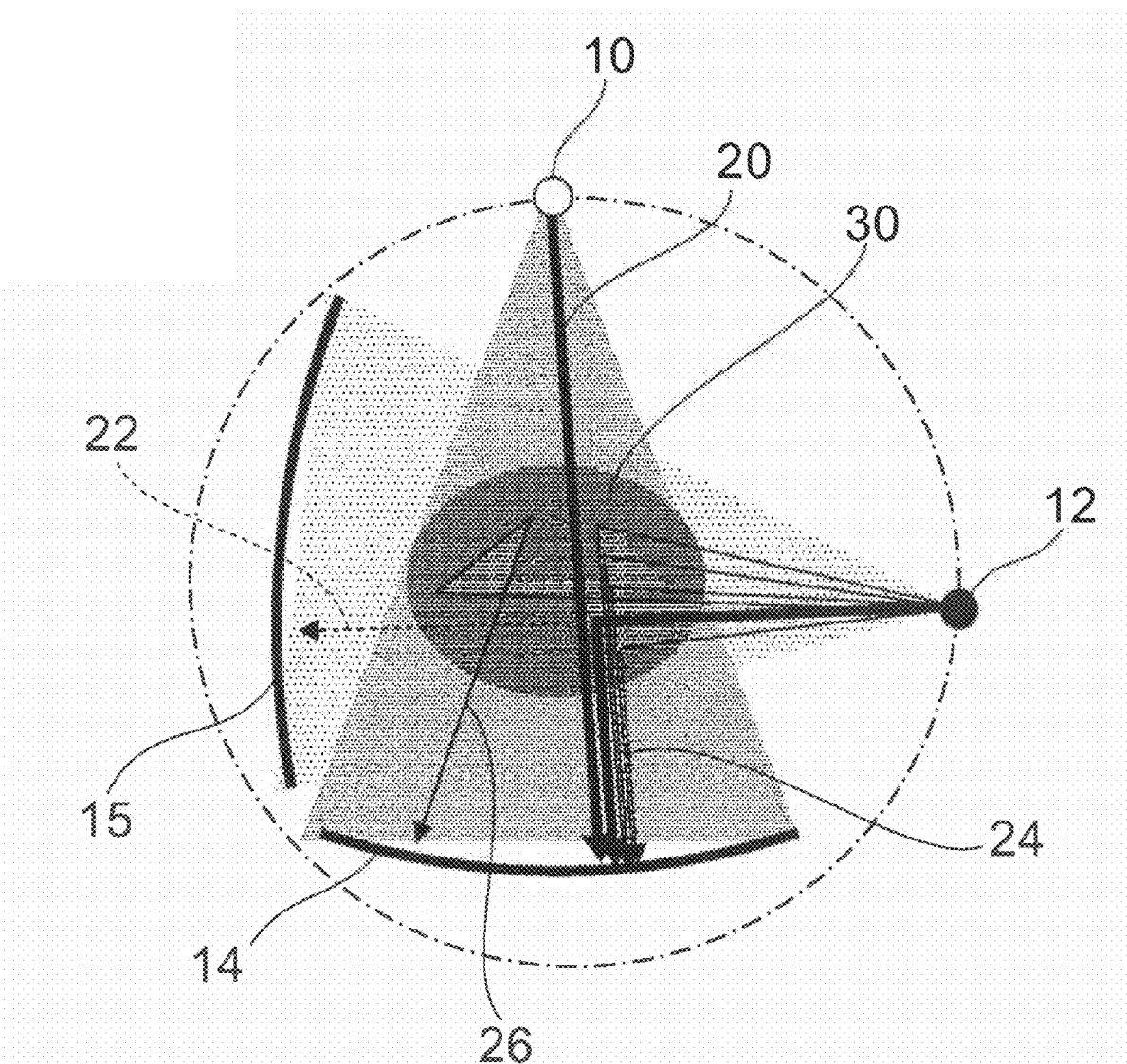
FIG. 2 is a schematic view describing scattering of X-rays in the interior of a subject.

FIG. 2 is a schematic view describing the scattering of X-rays in the interior of the subject 30.

The X-rays radiated radially from the second bulb 12 is scattered at every point in the subject 30 and reach the detector 14 as well as the transmission ray 24 from the first bulb 10. A multiply scattered ray 26 having a plurality of scatterings also reaches the detector 14. Assuming uniformity of a sectional structure of the subject 30 and neglecting the multiply scattered ray 26, an incident intensity distribution to the detector 14 is calculated for only the primary scattered ray 24 having only one scattering in the interior of the subject 30. Placing a detector 15 at a position opposite to the second bulb 12 also allows a transmission ray 22 from the second bulb 12 to be detected. It is noted that the subject 30 is assumed to be an elliptical shape to imitate a human body.

A calculation procedure of the scattered ray intensity distribution will be described.

Figure 3:
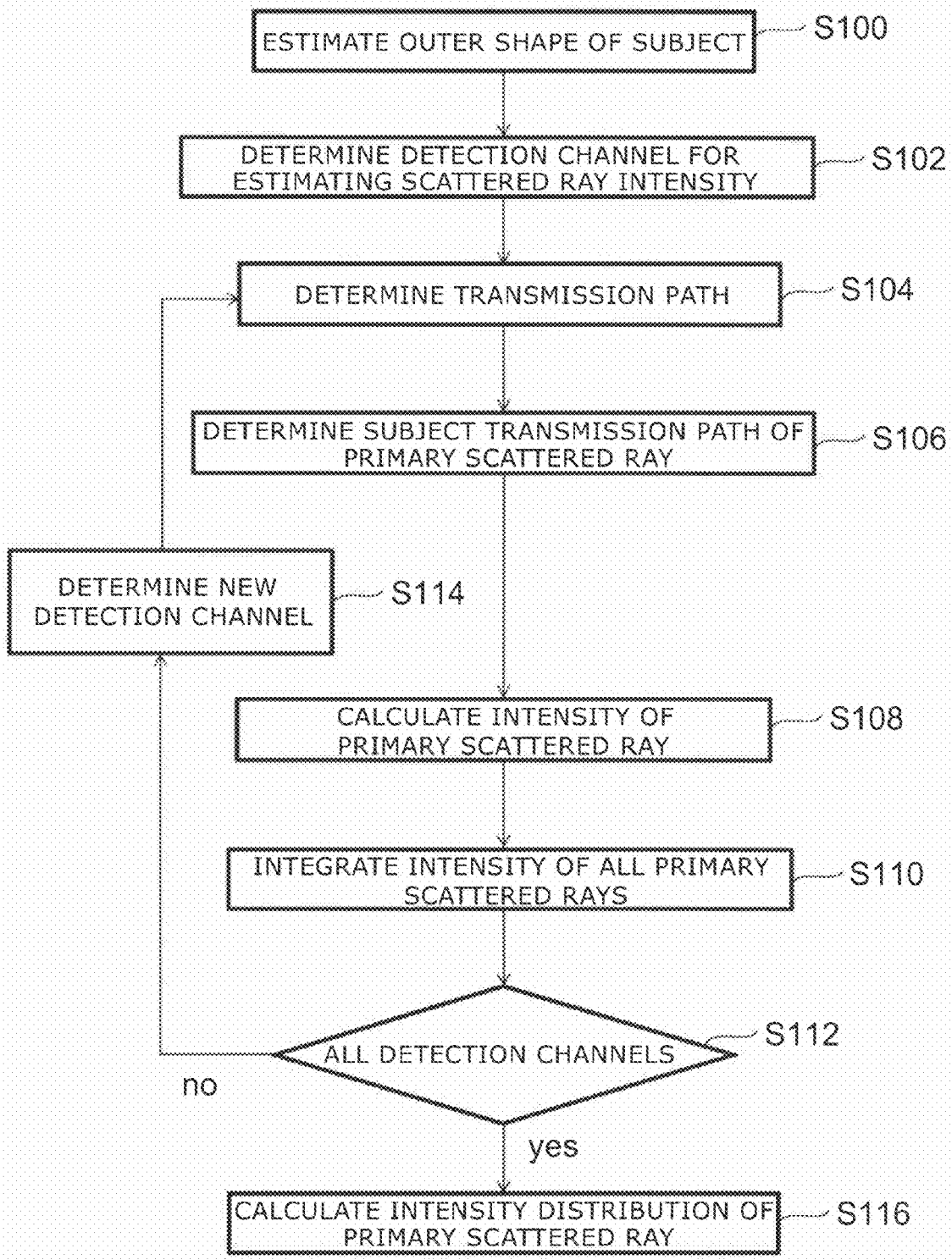
FIG. 3 is a flow chart illustrating a method for estimating the scattered ray intensity distribution of X-rays according to the embodiment of the invention.

FIG. 3 is a flow chart illustrating a method for estimating the scattered ray intensity distribution of the X-rays according to the embodiment of the invention.

The method for estimation of the embodiment includes estimating an outer shape of the subject (step S100), determining a detection channel for estimating the scattered ray intensity (step S102), determining a transmission path between the bulb and the detection channel (step S104), determining a subject transmission path of the primary scattered ray (step S106), calculating the intensity of the primary scattered ray (step S108), integrating the intensity of all primary scattered rays (step S110), judging whether integration of the primary scattered ray is performed or not for all detection channels (step S112), determining a new detection channel (step S114) and calculating the primary scattered ray intensity distribution on the detector (step S116).

Figure 4A:
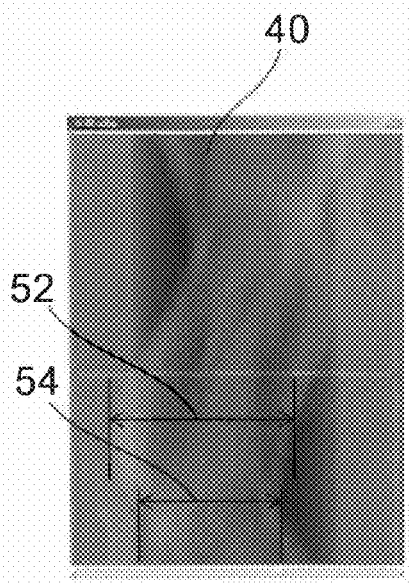
FIGS. 4A and 4B are data views for describing an estimation procedure of an outer shape of the subject 30.
Figure 4B:
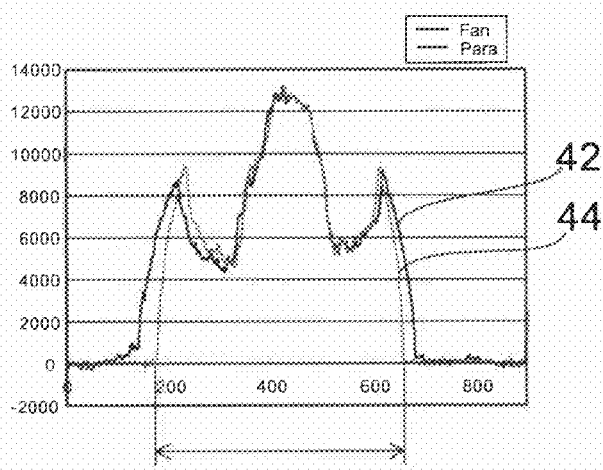
Figure 4B:
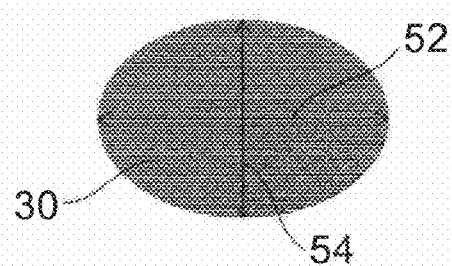

FIGS. 4A and 4B are data views for describing an estimation procedure of the outer shape of the subject 30 (step S100).

As shown in FIG. 4A, a projection data 40 of the subject 30 including the scattered rays is obtained. Next, as shown in FIG. 4B, a profile along channels on the detector 14 is achieved from the projection data 40. A major axis profile 42 and a minor axis profile 44 achieved with reference to a major axis 52 and a minor axis 54 of the subject 30 imitating an elliptic body represent an intensity associating with light and dark of the projection data 40. The major axis 52 and the minor axis 54 can be achieved from widths of profiles respectively.

FIGS. 5A to 5D are schematic views describing an estimation procedure of the scattered ray intensity.

Figure 5A:
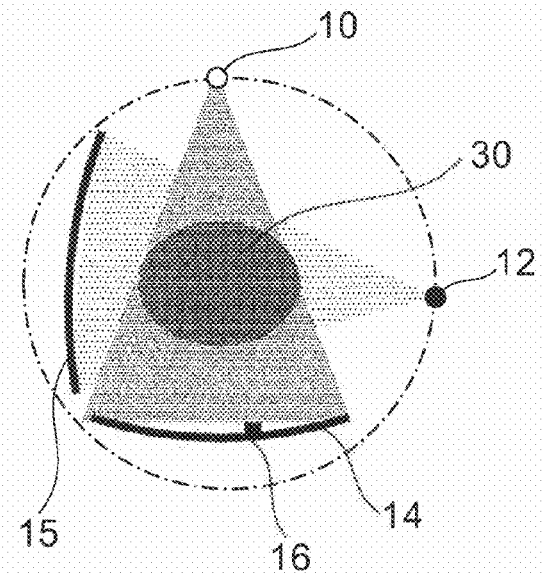
FIGS. 5A to 5D are schematic views describing an estimation procedure of scattered ray intensity.

FIG. 5A represents determining a detection channel 16 for estimating the scattered ray intensity (step S102) on the detector 14. The scattered ray intensity is estimated on each of all detection channels 16 arrayed on the detector 14, and the X-ray intensity distribution on the detector 14 is achieved by integrating them.

Figure 5B:
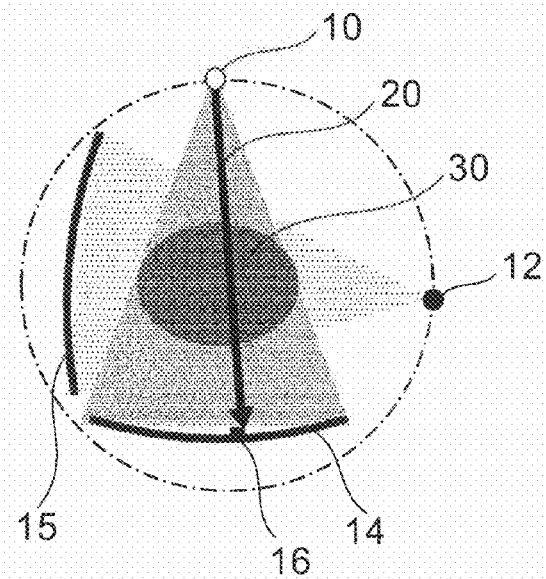

FIG. 5B represents determining the transmission path (step S104). Connecting the first bulb 10 and the detection channel 16 determines the transmission path of the X-rays to be detected. When the X-ray intensity radiated from the first bulb 10 is Io, assuming an X-ray absorption coefficient of the subject 30 to be μ and the transmission path length to be x' as shown in FIG. 1, the transmission ray intensity Ip to be detected by the detection channel 16 is given by a following equation.

$$Ip = Io \times \exp(-\mu x') \qquad (1)$$

Figure 5C:
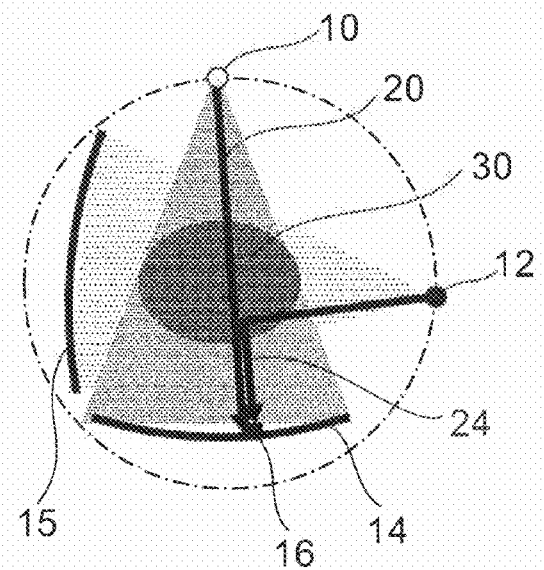

FIG. 5c represents determining the substrate transmission path of the primary scattered ray 24 (step S106) and calculating the intensity of the primary scattered ray 24 (step S108). Out of X-rays from the second bulb 12 provided imaginarily or experimentally, the transmission path of the primary scattered ray 24 having only one scattering in the interior of the subject 30 is achieved to calculate the scattered ray intensity Is to be detected by the detection channel 16. Assuming the X-ray intensity radiated from the second bulb 12 to be Io, the X-ray absorption coefficient of the subject 30 to be μ, the transmission path length to be x as shown in FIG. 1 and a scattering probability of X-ray to be P(θ), the scattered ray intensity Is is given by a following equation, $$Is = Io \times \exp(-\mu x) \times P(\theta) \qquad (2)$$

where θ is a scattering angle of the primary scattered ray shown in FIG. 1.

Figure 5D:
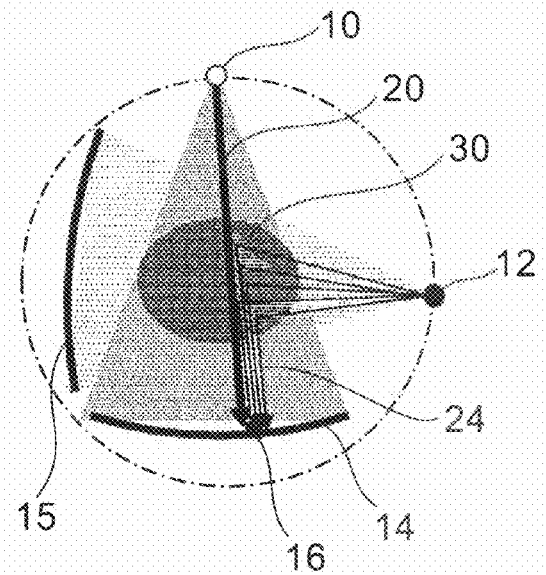

FIG. 5d represents integrating the intensity of all primary scattered rays 24 (step S110). As described above with reference to FIG. 1, the incidence angle βs of X-rays radiated from the second bulb 12 is, for example, varied every 0.1 degree and paths of all generated primary scattered rays are determined, and the scattered ray intensity Is of every primary scattered ray 24 to be detected by the channel 16 is integrated. At this time, the detection intensity I to be detected by the channel 16 is $I = Ip + \Sigma Is$.

As described above with reference to FIG. 1, performing from step S104 to step S110 for all detection channels 16 on the detector 14 while varying the angle βm of the X-rays radiated from the first bulb 10 allows the X-ray intensity distribution and the primary scattered ray intensity distribution on the detector 14 to be obtained.

Furthermore, reconfiguration of the projection data collected by rotating the first bulb 10 around the subject 30 enables a cross-sectional image (tomogram) to be obtained.

In this embodiment, the subject 30 is approximated to water, and estimation of the scattered ray intensity distribution can be performed using the X-ray scattering probability for water.

Figure 6:
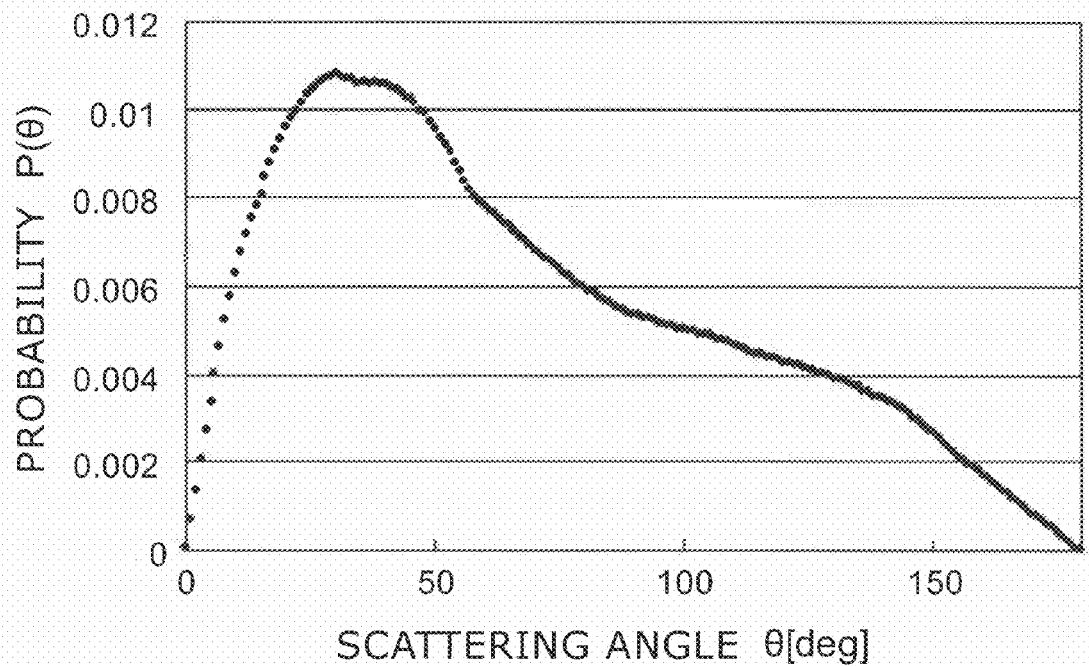
FIG. 6 is a graph view illustrating scattering probability $P(\theta)$ of X-rays for water.

FIG. 6 is a graph view illustrating the scattering probability P(θ) of X-ray for water. The scattering probability P(θ) can be calculated based on an X-ray spectra, a scattering angle and a material of the subject. ⊖ is the scattering angle of scattered X-rays with respect to the incident X-rays as described above with reference to FIG. 1.

Figure 7:
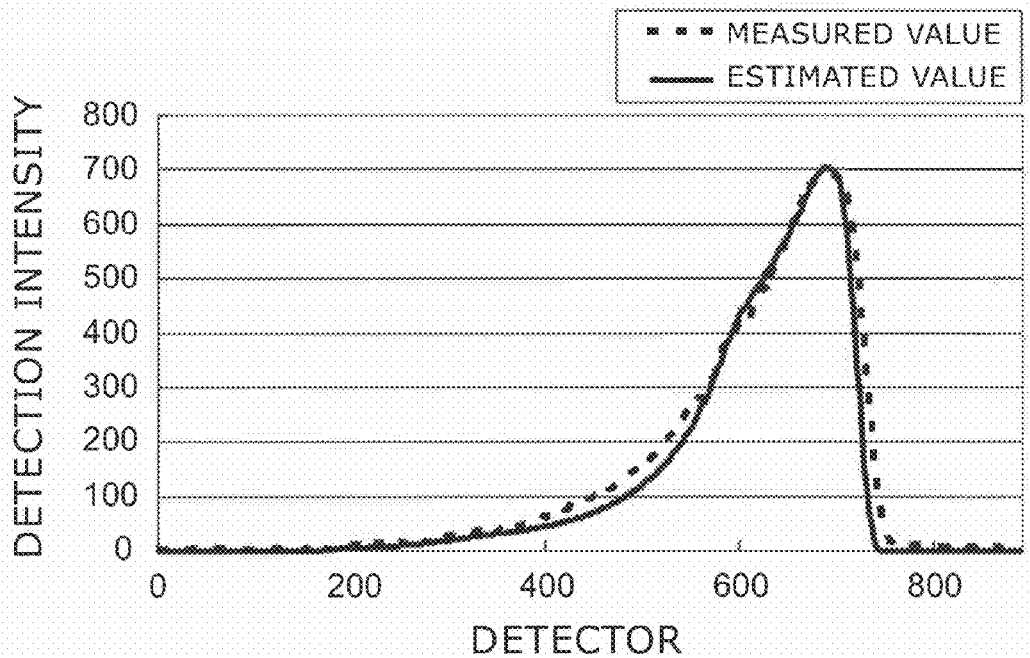
FIG. 7 is a graph view showing a comparison of a measured value to a estimated value of the scattered ray.

FIG. 7 is a graph view showing a comparison of the measured values to the estimated values for the scattered ray.

Assuming the subject 30 to be made of water, using the X-ray absorption coefficient for water as μ in equation (2) and the scattering probability P(θ) shown in FIG. 6, the scattered ray intensity Is has been obtained from equation (2). The estimated values ΣIs for all scattered rays are indicated by a solid line and the measured values are indicated by a broken line. The measured values are obtained on the detector 14 for the primary scattered rays 24 from the second bulb 12 provided. The horizontal axis represents a number of the detection channel 16 arrayed on the detector 14. The intensities on the vertical axis are coincided at a peak value. Distributions of the measured values and the estimated values on the detector 14 coincide extremely well.

In the above description, attention has been paid to the scattering from another second bulb 12 other than the first bulb 10 with regard to the scattering in the interior of the subject 30. This is because the scattered ray from another second bulb 12 other than the first bulb 10 has been supposed as a scattered ray normally incident to the detector 14 unable to be removed by a collimator. However, removal of the scattering in the interior of the subject 30 of X-rays from the first bulb 10 is also a problem for the X-ray CT apparatus. Particularly, when the detection channel becomes smaller from the viewpoint of improving a resolution, difficulty of providing the collimator increases, and necessity for the X-ray CT apparatus without the collimator arises. In that case, a method for removing the scattered ray from the first bulb 10 by calculation without use of devices provided on the apparatus is absolutely necessary.

According to this embodiment, in the X-ray CT apparatus, producing a ghost image on the cross-sectional image of the subject enables to calculate quickly and estimate the scattered ray component causing degradation of image quality.

Next, the X-ray CT apparatus according to the embodiment of the invention will be described.

Figure 8:
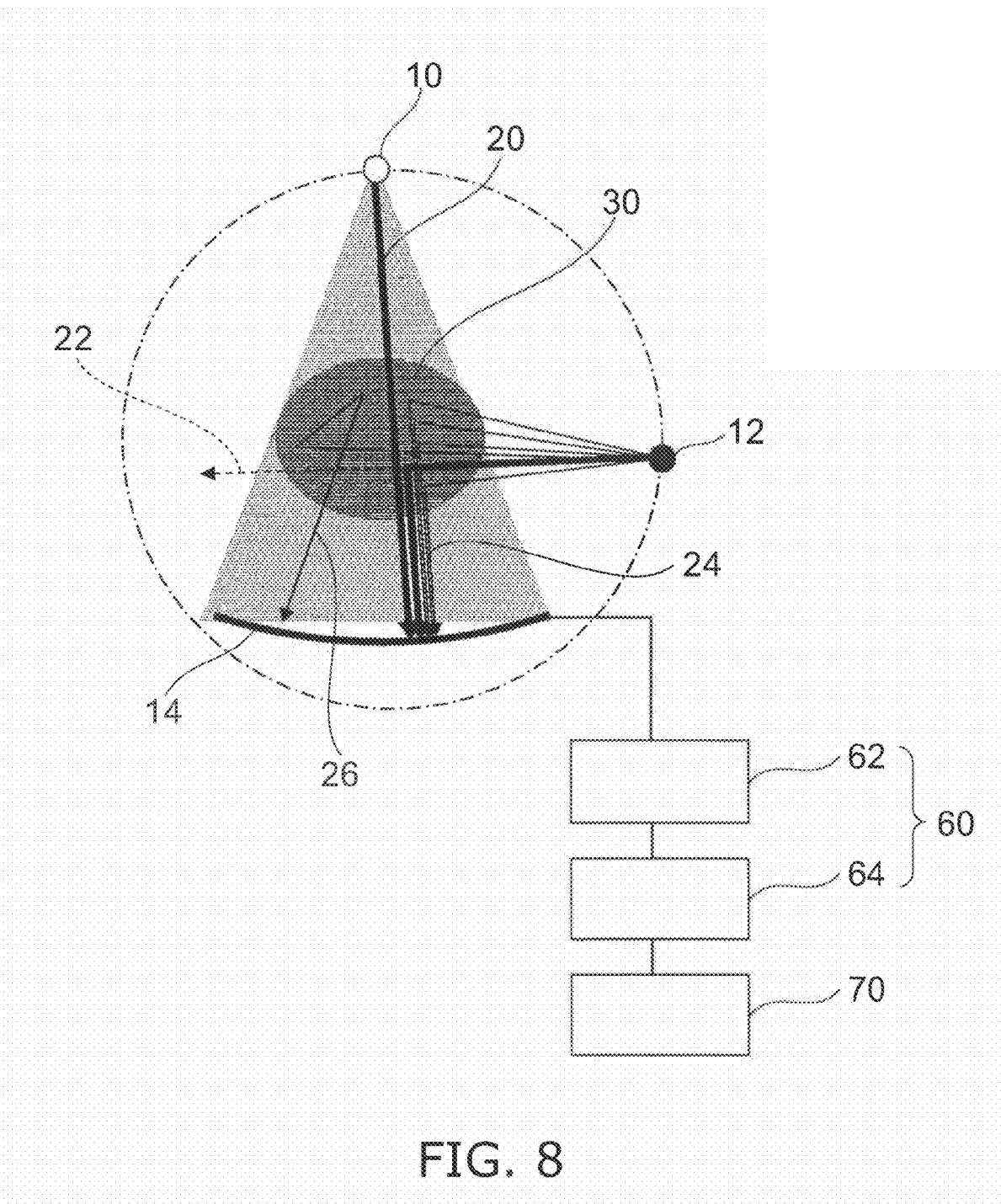
FIG. 8 is a schematic view illustrating an X-ray CT apparatus allowing the scattered ray intensity distribution to be estimated.

FIG. 8 is a schematic view illustrating the X-ray CT apparatus allowing the scattered ray intensity distribution to be estimated.

The X-ray CT apparatus of this embodiment is comprised of the first bulb (X-ray generation section) 10, the second bulb 12, the subject 30, the detector (X-ray detection section) 14, and a scattered ray calculation section 60 and an image reconfiguration section 70 connected to the detector 14.

The transmission ray 20 from the first bulb 10, and the multiply scattered ray 26 and the primary scattered ray 24 from the second bulb 12 are incident to the detector 14. The scattered ray calculation section 60 calculates the scattered ray intensity distribution using the method described above with reference to FIG. 1 to FIG. 7 for the X-ray scattered intensity distribution to be detected by the detector 14. That is, the scattered ray calculation section 60 includes a first calculation section 62 and a second calculation section 64. The first calculation section 62 calculates the path length of the scattered ray passing through the subject. The second calculation section 64 calculates the intensity of the scattered ray based on the path length, the X-ray absorption coefficient of the subject and the scattering probability by the subject.

On the basis of the scattered ray intensity distribution calculated like this, the X-ray intensity distribution is corrected with regard to the scattered ray component, and the image reconfiguration section 70 forms the cross-sectional image using the correction data.

The primary scattered ray 24 from all radiation sources (X-ray generation section) supposed to be as the second bulb 12 is calculated by the scattered ray calculation section 60, thus any scattering of the scattered ray from the radiation source can be corrected by the calculation. Moreover, a specific source for the scattered ray is provided, the X-ray intensity distribution including the scattering from the source is achieved on the detector 14, and thereby it is also possible that the scattered ray component is calculated by the scattered ray calculation section 60, the X-ray intensity distribution is corrected and the cross-sectional image without degradation of the image quality is reconfigured.

The embodiment of the invention has been described with reference to the examples. However, the invention is not limited to the examples described above.

That is, the invention is not limited to the examples, but can be variously modified without departing from the feature of the invention, and all of these are encompassed within the scope of the invention.

The invention claimed is:

1. A method for estimating a scattered ray intensity distribution in an X-ray CT apparatus, the method comprising:
   irradiating a subject with X-rays; and
   configuring a cross-sectional image of the subject by detecting the X-rays passing through the subject,
   on the basis of a path length of a scattered ray passing through the subject, an X-ray absorption coefficient of the subject and an X-ray scattering probability of the subject, intensity of the scattered ray being calculated.

2. The method for estimating the scattered ray intensity distribution according to claim 1, wherein a transmission path of the X-rays passing through the subject is determined.

3. The method for estimating the scattered ray intensity distribution according to claim 1, wherein the path length is calculated in the calculation of the intensity of the scattered ray.

4. The method for estimating the scattered ray intensity distribution according to claim 1, wherein intensity of a component scattered once of the scattered ray is calculated assuming uniformity of a sectional structure of the subject.

5. The method for estimating the scattered ray intensity distribution according to claim 1, wherein intensity of a component scattered once of the scattered ray in a direction of the path length is integrated.

6. The method for estimating the scattered ray intensity distribution according to claim 5, wherein intensity of the component integrated is calculated for all of the path lengths is calculated.

7. The method for estimating the scattered ray intensity distribution according to claim 1, wherein the intensity of the scattered ray is calculated under approximation of the subject to water.

8. The method for estimating the scattered ray intensity distribution according to claim 1, wherein the X-ray absorption coefficient is an X-ray absorption coefficient for water.

9. The method for estimating the scattered ray intensity distribution according to claim 1, wherein the X-ray scattering probability is an X-ray scattering probability for water.

10. The method for estimating the scattered ray intensity distribution according to claim 1, wherein a shape of the subject is reconfigured from a projection data including the scattered ray, and a path length in the subject is achieved from the shape.

11. The method for estimating the scattered ray intensity distribution according to claim 1, wherein the scattered ray is produced by irradiating the subject with X-rays generated from any of the plurality of X-ray generation sections.

12. An X-ray CT apparatus comprising:
a first X-ray generation section configured to generate X-rays;
an X-ray detection section configured to detect the X-rays passing through a subject;
an image reconfiguration section configured to configure a cross-sectional image of the subject on the basis of results detected by the X-ray detection section; and
a scattered ray calculation section configured to estimate a scattered ray intensity distribution of the X-rays in the subject,
the scattered ray calculation section estimating the scattered ray intensity distribution by calculating the intensity of the scattered ray on the basis of a path length of a scattered ray passing through the subject, an X-ray absorption coefficient of the subject and an X-ray scattering probability of the subject, and
the image reconfiguration section reconfiguring the cross-sectional image by correcting the results detected by the X-ray detection section using the scattered ray intensity distribution estimated by the scattered ray calculation section.

13. The X-ray CT apparatus according to claim 12, wherein the scattered ray calculation section calculates intensity of a component scattered once of the scattered ray assuming uniformity of a sectional structure of the subject.

14. The X-ray CT apparatus according to claim 12, wherein the scattered ray calculation section calculates the path length.

15. The X-ray CT apparatus according to claim 12, further comprising: a second X-ray generation section radiating X-rays,
the scattered ray being produced by irradiating the subject with X-rays generated from the second X-ray generation section.

16. The X-ray CT apparatus according to claim 12, wherein the X-ray detection section detects the X-rays generated from the first X-ray generation section to pass through the subject, and the scattered ray.

17. The X-ray CT apparatus according to claim 12, wherein the image reconfiguration section configures the cross-sectional image of the subject by reconfiguring a projection data achieved by rotating the first X-ray generation section around the subject.

18. The X-ray CT apparatus according to claim 12, wherein the scattered ray calculation section calculates the intensity of the scattered ray under approximation of the subject to water.

19. The X-ray CT apparatus according to claim 12, wherein the scattered ray calculation section calculates the intensity of the scattered ray using an X-ray absorption coefficient for water as the X-ray absorption coefficient.

20. The X-ray CT apparatus according to claim 12, wherein the scattered ray calculation section calculates the intensity of the scattered ray using a scattering probability for water as the scattering probability.

* * * * *